United States Patent

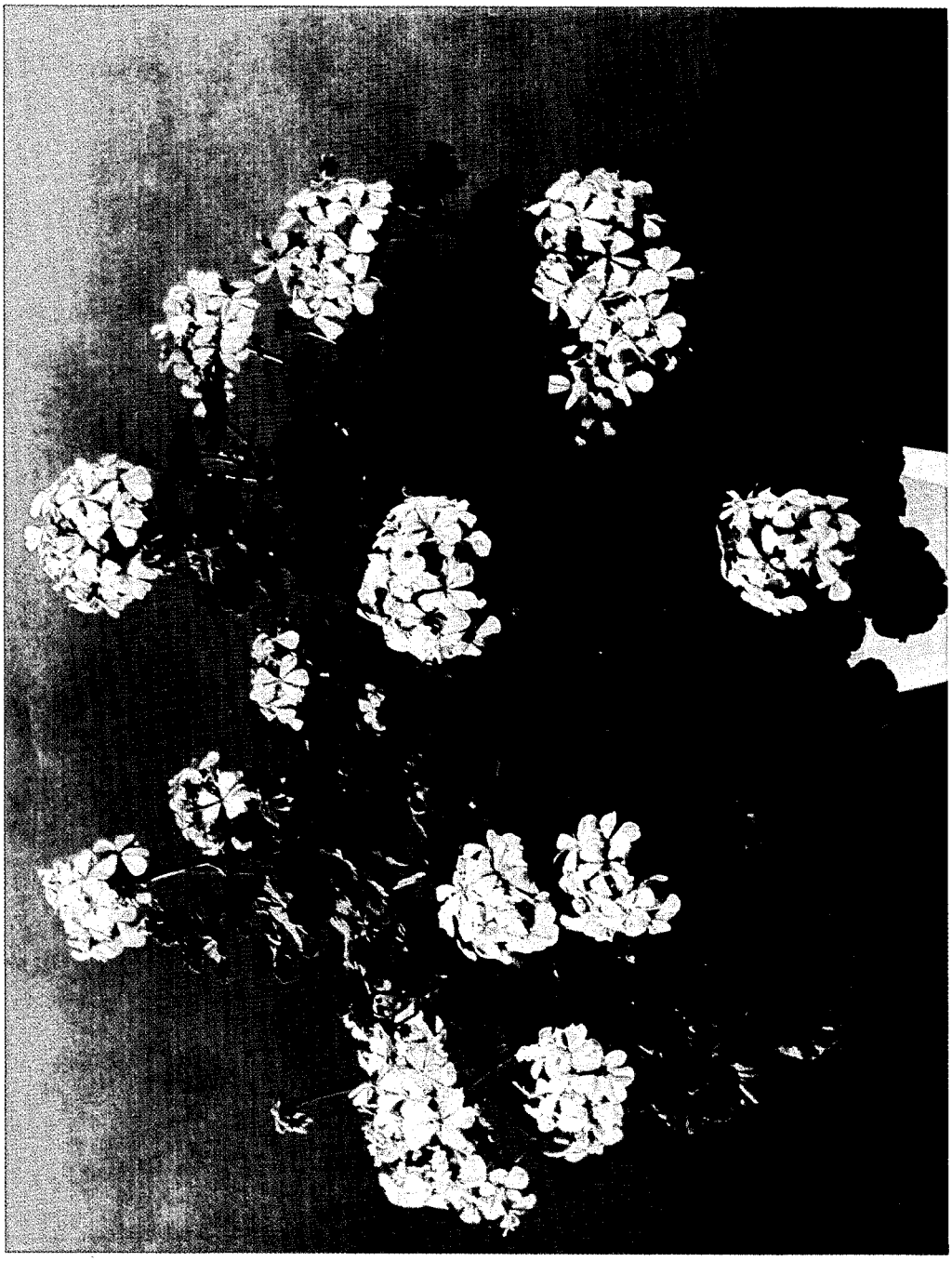

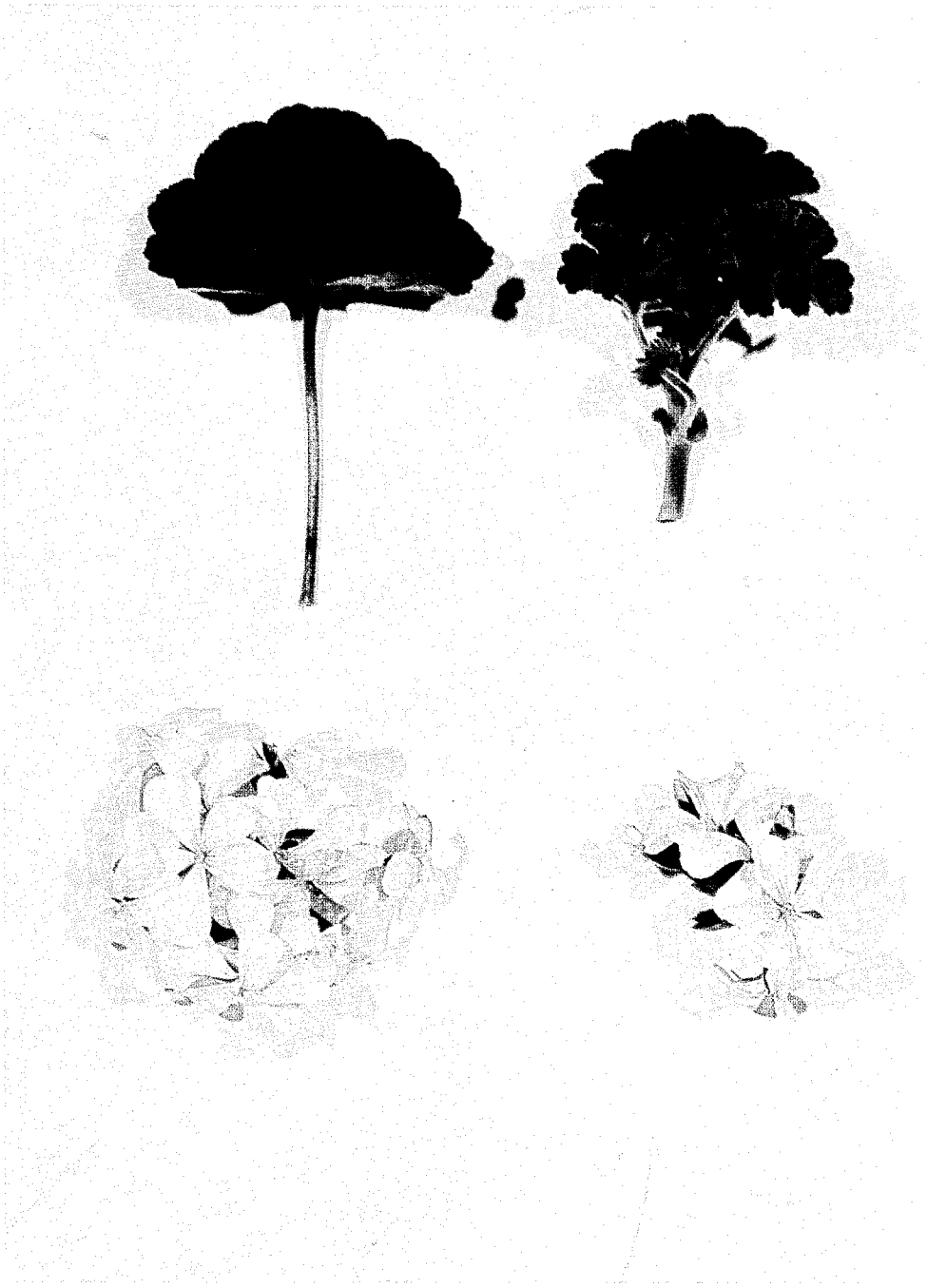

Plant Pat. 3,942

Patented Aug. 24, 1976

1

3,942
GERANIUM PLANT

William E. Duffett, Akron, Ohio, and Walter W. Knicely, Inwood, Va., assignors to Yoder Brothers, Inc., Barberton, Ohio

Filed June 20, 1975, Ser. No. 588,849
Int. Cl.[2] A01H *5/00*
U.S. Cl. Plt.—68 1 Claim

The present invention comprises a new and distinct cultivar, a hybrid of the genus Pelargonium, L'Her., hereinafter referred to by the cultivar name Coy Cherub (#69070001).

Coy Cherub was originated from a cross made under the supervision of William E. Duffett and Walter W. Knicely in a controlled breeding program in Barberton, Ohio in the year 1968.

The female, or seed parent, was #565–A (unnamed seedling). The male, or pollen parent, was a fourth generation inbred selection of Madonna (unpatented, commercially available). Both parents were products of the breeding program of the present inventors.

Coy Cherub was discovered and selected as a flowering seedling within the progeny of the stated cross by William E. Duffett and Walter W. Knicely on Sept. 26, 1969 in an outdoor field environment in Barberton, Ohio.

Coy Cherub is a product of a planned breeding program which had the objective of creating durable, disease tolerant geraniums that would fulfill in part or in whole the need for a geranium with compact and spreading growth habit, vibrant flower color, fast spring pot response period, and prolific flowering traits under outdoor summer conditions in Ohio.

The first act of asexual reproduction of Coy Cherub was accomplished when vegetative cuttings were taken from the initial selection in October 1969, in Barberton, Ohio, by a technician under formulations established and supervised by William E. Duffett and Walter W. Knicely.

Continued asexual reproduction by vegetative cuttings for evaluative tests in flowering and stock programs in conjunction with horticultural certification initiated July 27, 1971, by William E. Duffett and Walter W. Knicely have demonstrated that the combination of characteristics as herein disclosed for Coy Cherub are firmly fixed and are retained through successive generations of asexual reproduction.

The following descriptive observations, measurements, and comparisons were derived from plants grown both in a greenhouse and under outdoor field conditions. The greenhouse-grown, spring flowering containerized plants were planted in an outdoor field in late May, early June and observed during the summer and fall months. The environmental conditions under which the observed plants were grown are generally described in local Climatological Data, Annual Summary With Comparative Data, Akron, Ohio, U.S. Department of Commerce, National Oceanic and Atmospheric Administration, Environmental Data Service, Washington, D.C., 1970, 1971, 1972, 1973, 1974. General cultural practices utilized closely approximate those generally used in commercial practice and are described in Chart A, attached at the end of the present specification.

The following traits have been repeatedly observed and are determined to be basic characteristics of Coy Cherub which in combination distinguish this geranium as a new and distinct cultivar:

(1) Light salmon pink flower color with minimal color oxidation.

(2) Compact, spreading growth habit.

(3) Prolific flowering traits under Ohio outdoor summer conditions.

2

(4) Durable flower and foliage under Ohio outdoor summer conditions.

(5) Fast spring pot flowering response.

The accompanying photographic drawings show typical flower and foliage characteristics of Coy Cherub. Sheet 1 illustrates Coy Cherub in bloom, and Sheet 2 comprises a photograph showing the development of the inflorescence and the foliage of Coy Cherub. It is noted that difficulty was encountered in obtaining photographs accurately representing the true colors of Coy Cherub. The actual flower color of Coy Cherub is closely approximated in Sheet 1, and the foliage color of Coy Cherub is closely approximate in Sheet 2. The color readings are, however, correct.

The phenotype of Coy Cherub may vary significantly with variations in environment such as temperature, light intensity, and daylength. The genotype of Coy Cherub was not observed under all possible environments.

Of the many commercial cultivars known to the present inventors, the most similar cultivars in comparison to Coy Cherub are Dawn (unpatended) and Pink Camelia (unpatented). Reference is made to attached Chart B which compares certain characteristics of Coy Cherub and the noted cultivars. General comparisons are as follows:

(1) In comparison to Dawn, Coy Cherub has lighter salmon pink flower color, shorter height, and less prolific flowering traits under outdoor summer Ohio conditions. The semi-spreading growth habit, early spring flowering response and the outdoor flower and foliage durability of Coy Cherub are similar to those of Dawn.

(2) In comparison to Pink Camelia, Coy Cherub has lighter salmon pink flower color with greater color retention, shorter height, and less prolific flowering traits under outdoor summer Ohio conditions. The semi-spreading growth habit, early spring flowering response and the outdoor flower and foliage durability of Coy Cherub are similar to those of Pink Camelia.

In the following description, color references are to the Munsell Limit Color Cascade, 1972 edition. Color values were determined between 4:00 p.m. and 4:30 p.m. on July 24, 1974, under 150 foot candle light intensity at Barberton, Ohio.

BOTANICAL CLASSIFICATION

A hybrid of the genus Pelargonium, L'Her., cv Coy Cherub.

I. Inflorescence

A. Umbel:
- *Average diameter.*—3.3 inches.
- *Average depth.*—2.5 inches.
- *Peduncle.*—Ranges from 4.5 inches to 7.3 inches in length, averaging 6.3 inches.
- *Pedicel.*—0.8 inch to 1.5 inches in length.

B. Corolla:
- *Average diameter.*—1.3 inches.
- *Type.*—Single; rotate.
- *Color.*—Abaxial: 37–4, Adaxial: 37–2.

C. Bud:
- *Shape.*—Conodial.
- *Color.*—Abaxial: 37–4. Adaxial: 37–2.

D. Reproductive organs:
- *Androecium.*—Stamen: Monodelphous, dorsifixed; pentadynamous. Pollen: Present.
- *Gynoecium.*—Stigma: 5-lobed; linear. Carpel: 5 locules; pubescent.

E. Response period: Early. 80% of plants in plot had at least 1 flower open on May 30, 1974, from a direct stick date of Apr. 3, 1974 (8 weeks).

F. Production: Good.

| Date: | Average number of flowers per plant |
|---|---|
| July 15, 1974 | 1.9 |
| Aug. 1, 1974 | 2.0 |
| Aug. 15, 1974 | 4.0 |
| Sept. 1, 1974 | 3.8 |

G. Durability:

*Shatter resistance.*—Good.

*Tolerance of botrytis.*—Good.

II. Plant

A. Foliage:

*Form.*—Reni-form.

*Margin.*—Undulate; crenate.

*Color.*—Abaxial: Between 21–15 and 21–16. Adaxial: Approximately 21–15 but more grey. Zonation: Approximately 21–16.

*Durability (outdoor).*—Good.

B. Growth habit:

*Form.*—Semi-spreading.

*Height.*—Short, semi-dwarf.

*Internode length.*—Short.

C. Durability:

*Tolerance of botrytis.*—Good.

CHART A—ENVIRONMENTS FOR GERANIUM PERFORMANCE EVALUATION COMMONLY USED IN BARBERTON, OHIO

| | Environment | |
|---|---|---|
| | I. Greenhouse | II. Outdoor field |
| Period of year | April through May | June through September |
| Temperature (° F.) | Night: 62–65; Bright day; 72–75; Cloudy day; 68–70 | Uncontrolled dependent upon prevailing weather conditions. |
| Light | Uncontrolled dependent upon natural daylength and light intensity. Light shade compound on greenhouse class. | Uncontrolled dependent on natural daylength and light intensity. |
| Schedule and specifications | Take vegetative cutting: April 2. Cutting Specifications: 2–2.75 inches in length. Direct stick: April 3; 1 cutting per 4 inch plastic pot. Media: 1 part soil, 1 part peat, 1 part perlite. Move to 6″ x 7″ spacing: April 23. Flower date: May 28. | Plant: early June (product produced in I). Location: outdoor field. Media: well drained field soil. |

CHART B—COMPARISON OF COY CHERUB WITH DAWN AND PINK CAMELIA

| Cultivar | Flower color | Growth habit | Height | Spring flowering response period | Outdoor flower production | Outdoor flower durability | Outdoor foliage durability |
|---|---|---|---|---|---|---|---|
| Coy Cherub | Light salmon pink | Semi-spreading | Semi-dwarf | Early | Prolific | Good | Good. |
| Dawn | Salmon pink | do | Medium | do | Very prolific | do | Do. |
| Pink Camelia | Salmon pink bicolor | do | Short | do | do | do | Do. |

NOTE.—Comparisons made of plants grown in a greenhouse and in an outdoor field in Barberton, Ohio under cultural conditions as described in Chart A.

We claim:

1. A new and distinct cultivar of geranium plant characterized particulary as to uniqueness by the combined characteristics of light salmon pink flower color with minimal color oxidation; compact, spreading growth habit; prolific flowering traits under Ohio outdoor summer conditions; durable flower and foliage under Ohio outdoor summer conditions, and fast spring pot flowering response.

No references cited.

ROBERT E. BAGWILL, Primary Examiner